United States Patent
Hayden

(10) Patent No.: US 9,382,582 B1
(45) Date of Patent: Jul. 5, 2016

(54) METHODS, COMPOSITIONS AND KITS FOR ENRICHING FOR A MINOR TEMPLATE AMPLIFICATION PRODUCT IN A MIXED TEMPLATE AMPLIFICATION REACTION

(71) Applicant: Tracy Hayden, San Francisco, CA (US)

(72) Inventor: Tracy Hayden, San Francisco, CA (US)

( * ) Notice: Subject to any disclaimer, the term of this patent is extended or adjusted under 35 U.S.C. 154(b) by 0 days.

(21) Appl. No.: 14/834,710

(22) Filed: Aug. 25, 2015

(51) Int. Cl.
*C12P 19/34* (2006.01)
*C12Q 1/68* (2006.01)

(52) U.S. Cl.
CPC ............ *C12Q 1/6853* (2013.01); *C12Q 1/6888* (2013.01); *C12Q 2600/156* (2013.01)

(58) Field of Classification Search
USPC .............................................. 435/6.12, 91.2
See application file for complete search history.

(56) References Cited

U.S. PATENT DOCUMENTS 8,361,753 B2 * 1/2013 Zon ...................... C12Q 1/6848 435/6.1
2009/0270264 A1 * 10/2009 Overson .................. C40B 20/06 506/5

OTHER PUBLICATIONS

Lebedev et al., Nucleic Acids Research 36(20), e131, pp. 1-18 (2008).*

Elena Hidalgo Ashrafi, Natasha Paul "Improved PCR specificity with Hot Start PCR primers," (2009) BioTechniques 47:7789-7790.

Quin Chou, Marion Russell, David E. Birch, Jonathan Raymond, Will Bloch, "Prevention of pre-PCR mis-priming and primer dimerization improves low-copy-number amplifications," (1992) Nucleic Acids Research 20 (7):1717-1723.

Alexandre V. Lebedev, Natasha Paul, Joyclyn Yee, Victor A. Timoshchuk, Jonathan Shum, Kei Miyagi, Jack Kellum, Richard I. Hogrefe, Gereald Zon, "Hot Start PCR with heat-activatable primers: a novel approach for improved PCR performance," (2008) Nucleic Acids Research 36(20): e131.

Jonathan Shum, Natasha Paul, "Chemically modified primers for improved multiplex PCR," (2009) Analytical Biochemistry 388(2):266-272.

Severine Vuichard, Urs Borer, Michel Bottinelli, Christian Cossu, Naseem Malik, Verena Meier, Christian Gehrig, Andrea Sulzer, Marie-Laure Morerod, Vincent Castella, "Differential DNA extraction of challenging sexual-assualt samples: a Swiss collaborative study," (2011) Investigative Genetics 2:11.

* cited by examiner

*Primary Examiner* — Kenneth Horlick

(57) ABSTRACT

A longstanding challenge in forensics is resolving the genetic profile of a minor contributor in a mixed contributor sample. The instant disclosure provides for differentially labeling the products resulting from the amplification of a template from a major contributor relative to that of a minor contributor. Based on this differential labeling, the genetic profile of the minor contributor can be resolved from that of a major contributor.

6 Claims, No Drawings

METHODS, COMPOSITIONS AND KITS FOR ENRICHING FOR A MINOR TEMPLATE AMPLIFICATION PRODUCT IN A MIXED TEMPLATE AMPLIFICATION REACTION

RELATED APPLICATIONS

None

BACKGROUND

Short tandem repeat (STR) DNA sequences are interspersed throughout the human genome. These loci are highly polymorphic with respect to the number of repeat units they contain and may vary in internal structure as well. Variation in the number of STR repeat units at a particular locus causes the length of the DNA at that locus to vary from allele to allele.

While the alleles at a single STR locus may be the same for two different individuals in a population, especially if the individuals are genetically related, the probability that the alleles of any two unrelated individuals will be identical at several different STR loci becomes smaller and smaller as the number of loci examined increases. By determining the alleles at a sufficiently large number of STR loci it becomes possible to establish with virtual certainty whether or not two biological samples came from the same individual.

In forensic casework, it is common to encounter evidence samples, like vaginal swabs from a rape victim, which contain a high concentration of DNA from one source, the victim of rape, and only a small concentration of DNA from the perpetrator(s). In such instances the analyses of autosomal DNA will likely result in the perpetrator's autosomal STR profile being masked by the presence of the victim's DNA present in the mixture. This is problematic since the most prevalent DNA criminal databases rely largely on autosomal STR loci for individual identification.

The instant disclosure offers solutions to the challenge of determining the autosomal STR profile of a perpetrator in the presence of excess victim's DNA as well as other challenges.

BRIEF SUMMARY

The detection of an amplification product from a relatively minor template species in a sample with multiple template species is often of interest. However, the detection of these minor templates is hampered by interference from the predominant template. In nucleic acid amplification procedures, such as polymerase chain reaction (PCR), the predominate amplicon tends to be derived from the major template. This tendency can render detection of the minor template derived product problematic.

Disclosed herein are methods, compositions and kits of components for increasing the detectability of an amplification product from a minor template in a mixed template nucleic acid sample.

Accordingly, in some embodiments a method is disclosed, the method encompassing contacting a mixed sample, encompassing a major template and a minor template, with a first oligonucleotide primer and a second oligonucleotide primer, the first and the second oligonucleotides primers priming amplification from the same target sequence and the first, the second, or both the first and the second oligonucleotide primers encompassing a modification. A nucleic acid amplification reaction is performed and a reacted mixed sample results. The reacted mixed sample encompasses an amplicon from the minor template and an amplicon from the major template, wherein the amplicon from the minor template is more readily detected or more readily separated from the amplicon of the major template relative to a reacted sample from a nucleic acid amplification reaction with only the first oligonucleotide primer or the second oligonucleotide primer is present without a modification.

In some embodiments a composition is disclosed, the composition encompassing a first oligonucleotide primer, a second oligonucleotide primer and a third oligonucleotide primer. The first and the second oligonucleotide primers encompassing the reverse complement of the same nucleic acid sequence. The third oligonucleotide primer forms a primer pair with both the first oligonucleotide primer and the second oligonucleotide primer. At least one of the oligonucleotide primers is modified. At least one of the oligonucleotide primers is labeled. In some embodiments, the same oligonucleotide primer is both labeled and modified. In some embodiments, the composition encompasses an amplicon derived from the major template and an amplicon from the minor template, wherein the amplicon from the minor template is more readily detected or more readily separated from the amplicon of the major template relative to a composition with only the third oligonucleotide primer and the first oligonucleotide primer or the second oligonucleotide primer wherein the first oligonucleotide primer and the second oligonucleotide primer are not modified. In some embodiments, the composition also includes a mixed sample with a minor template and a major template.

In some embodiments, the molar concentration of the first oligonucleotide primer is at least 2-fold greater than the molar concentration of the second oliogonucleotide primer. In other embodiments, the molar concentration of the second oligonucleotide primer is at least 2-fold greater than the molar concentration of the first oliogonucleotide primer.

In some embodiments, a kit of parts is disclosed. The kit encompasses a first and a second oligonucleotide primer. The first and second oligonucleotide primer each prime DNA synthesis from the same target sequence but are distinguishable. In some embodiments, the second primer possesses a modification group which is thermally labile and limits polymerase mediated extension prior to the thermally mediated dissociation of the modification group. In some embodiments, the 3' terminal internucleotide linkage with the penultimate nucleotide of the second primer is modified by a 4-oxo-1-pentyl phosphotriester. In some embodiments, the 3' terminal internucleotide linkage with the penultimate nucleotide of the second primer is modified by a 2-(N-formyl-N-methyl)aminoethyl. In some embodiments, both the first and the second oligonucleotide primer each prime DNA synthesis from a sequencing flanking a short tandem repeat locus. In some embodiments, the second oligonucleotide primer is fluorescently labeled. In some embodiments, the kit also includes a polymerase.

These and other embodiments will be disclosed in more detail below.

DESCRIPTION OF THE DRAWINGS

None

DETAILED DESCRIPTION

The detection of the amplification product of a minor template is often of interest. In fields as diverse as medical diagnostics, microbial ecology and forensics there exists a need to identify the genetic signature of a minor template in the presence of an excess of a predominate template.

The presence of excess nucleic acid template from one source relative to another in a nucleic acid amplification reaction creates challenges in detecting the amplification product from the less abundant template. Nucleic acid amplification reactions are performed generally using limiting amounts of reagents. An excess of a major template competes for and consumes limiting reagents. As a result, amplification from the less abundant template can be less robust and methods may not be sensitive enough to detect or distinguish the product of the less abundant template from that of the major template.

A way to resolve amplicons derived from a major template and a minor template in a mixed template amplification reaction is to include reactants that are differentially used during the reaction. In such a reaction, one reactant is more prevalent in the amplification product (amplicon) from one template than the other. A method to accomplish this differential reactant inclusion is disclosed.

In some embodiments, the method entails the inclusion of oligonucleotide primers that hybridize to the same target nucleic acid sequence but are nonetheless differentially included or extended by a polymerase in an amplification reaction. An "oligonucleotide primer" is an isolated nucleic acid that can selectively hybridize to a reverse complementary nucleic acid strand and allows for template directed synthesis of a polynucleotide. The synthesis can take place in the presence of an appropriate enzyme, cofactor and substrates.

Oligonucleotide primers can be mechanically synthesized. During cellular DNA replication short, newly produced DNA polynucleotides are formed. These naturally occurring DNA polynucleotides are called Okazaki fragments. Mechanically synthesized oligonucleotide primers can differ from these naturally occurring Okazaki fragments by the absence of a 5' phosphate or by the presence of modifications, such as a label. Often the label is covalent bound to a nucleotide or internucleotide bonds by chemical linkages not present in naturally occurring nucleic acids. These differences render mechanically synthesized primers chemically and functionally distinct from Okazaki fragments. For instance, the absence of a 5' phosphate would preclude the ligation of Okazaki fragments. And Okazaki fragments can contain ribonucleic acids (RNA).

In some instances, the oligonucleotide primer is a modified oligonucleotide primer. A "modified oligonucleotide primer" is an oligonucleotide primer having at least one modification group. A "modification group" is a chemical moiety attached to an oligonucleotide primer. In certain embodiments, the chemical moiety is an ester.

In some embodiments a method is disclosed, the method encompassing contacting a mixed sample with a first oligonucleotide primer and a second oligonucleotide primer, the first and second oligonucleotides primers priming amplification of a same target sequence with the second oligonucleotide primer being modified and less efficacious at priming an amplification reaction than the first oligonucleotide primer. Performing a nucleic acid amplification reaction and thereby forming a reacted sample and detecting an amplicon derived from a minor template. In some embodiments, the reacted mixed sample is subjected to a fractionation technique. In some embodiments, the fractionation technique is electrophoresis. In other embodiments, the fraction technique is mass spectrometry.

In some instances the oligonucleotide primer which encompasses one or more modification groups has reduced efficacy for nucleic acid extension. In some instances, a modified oligonucleotide primer is at least 50% less efficacious at priming an amplification reaction than a corresponding oligonucleotide that lacks a modification, at least 60% less efficacious, at least 70% less efficacious, at least 80% less efficacious, a least 90% less efficacious, and even 95% less efficacious at priming an amplification reaction than its corresponding oligonucleotide primer lacking a modification. In some embodiments, the modification group precludes, or limits by at least 60%, at least 70%, at least 80%, at least 90%, at least 95% polymerase mediated extension of the oligonucleotide primer until the modification dissociates from the oligonucleotide primer.

Modified oligonucleotides primers include an oligonucleotide primer containing a modified nucleoside, an oligonucleotide primer containing a modified internucleotide linkage, or an oligonucleotide primer having any combination of modified nucleosides and modified internucleotide linkages.

In some embodiments a method is disclosed, the method encompassing contacting a mixed sample with a first oligonucleotide primer and a second oligonucleotide primer, the first and second oligonucleotides primers priming amplification from a same target sequence with the second oligonucleotide primer being modified and less efficacious at priming an amplification reaction than the first oligonucleotide primer. The modification of the second oligonucleotide primer can be a modified internucleotide linkage or a modified nucleotide or both. Performing a nucleic acid amplification reaction and thereby forming a reacted sample and detecting an amplicon from a minor template. In some embodiments, the reacted mixed sample is subjected to a fractionation technique. In some embodiments, the fractionation technique is electrophoresis. In other embodiments, the fraction technique is mass spectrometry.

In some instances, the modified oligonucleotide primer losses the modification during the amplification reaction. In an amplification reaction where two oligonucleotide primers possessing the same nucleotide sequences, with one oligonucleotide primer being modified and the other not, initially relatively more amplicons would incorporate the originally unmodified oligonucleotide primer when the modified oligonucleotide primer is less efficient at priming amplification. As the amplification reaction proceeds, the modification is lost and the originally modified oligonucleotide primer efficiently primes the amplification reaction. In such instances, the relative incorporation of the originally modified oligonucleotide primer in amplicons increases.

In some embodiments a method is disclosed, the method encompassing contacting a mixed sample with a first oligonucleotide primer and a second oligonucleotide primer, the first and second oligonucleotides primers priming amplification of a same target sequence with the second oligonucleotide primer being modified and less efficacious at priming an amplification reaction than the first oligonucleotide primer. Performing a nucleic acid amplification reaction, thereby forming a reacted sample wherein the second oligonucleotide primer losses the modification during the amplification reaction and detecting an amplicon from a minor template. In some embodiments, the reacted mixed sample is subjected to a fractionation technique. In some embodiments, the fractionation technique is electrophoresis. In other embodiments, the fraction technique is mass spectrometry.

An example of modified oligonucleotide primers are those possessing thermolabile modifications. These thermolabile modifications impair DNA polymerase mediated extension. This impairment is released by exposing the modified oligonucleotide primer to an elevated temperature for a sufficiently long period of time such that the modification is lost. Once the modification to the oligonucleotide primer is lost, DNA polymerase mediated extension can occur from the once modified oligonucleotide primer in earnest.

In some embodiments a method is disclosed, the method encompassing contacting a mixed sample with a first oligonucleotide primer and a second oligonucleotide primer, the first and second oligonucleotides primers priming amplification of a same target sequence with the second oligonucleotide primer having a thermolabile modification. Performing a nucleic acid amplification reaction, thereby forming a reacted sample and detecting an amplicon from a minor template. In some embodiments, the reacted mixed sample is subjected to a fractionation technique. In some embodiments, the fractionation technique is electrophoresis. In other embodiments, the fraction technique is mass spectrometry.

In some embodiments a method is disclosed, the method encompassing contacting a mixed sample with a first oligonucleotide primer and a second oligonucleotide primer, the first and second oligonucleotides primers priming amplification of a same target sequence with the second oligonucleotide primer having a thermolabile modification. Performing a nucleic acid amplification reaction, thereby forming a reacted sample wherein the second oligonucleotide primer losses the modification during the amplification reaction and detecting an amplicon from a minor template. In some embodiments, the reacted mixed sample is subjected to a fractionation technique. In some embodiments, the fractionation technique is electrophoresis. In other embodiments, the fraction technique is mass spectrometry.

In some instances, partial or complete dissociation of the modification group occurs after incubation, at or above 80° C., with $t_{1/2}$ between about 0.1-120 minutes but can occur between about 1-120 minutes, 2-90 minutes, between about 2-60 minutes, between about 2-40 minutes, between about 2-30 minutes, between about 2-5 minutes, at about 20, 19, 18, 17, 16, 15, 14, 13, 12, 11, 10, 9, 8, 7, 6, 5, 4, 3 or 2 minutes. In other embodiments, dissociation occurs in respect to temperature and does not require enzymes, chemicals, or amplification reaction conditions such as pH.

Modified oligonucleotide primers can have two states. The first state of the modified oligonucleotide primer is a reduced activity or an inactive state due to the presence of a modification group until the initial denaturation temperature is reached, 80° C., 85° C., 90° C., or 95° C. Upon reaching the initial denaturation temperature and with sufficient time, the oligonucleotide primer becomes relatively more active or active by thermally induced intramolecular fragmentation which converts the oligonucleotide to the second state. This second state of the oligonucleotide primer is the corresponding unmodified oligonucleotide primer which has an active state phosphodiester bond and is extendable by polymerase. Dissociation of the modification group occurs at approximately 80° C., 85° C., 90° C., or 95° C. between about 0.1-120 minutes, or between about 1-120 minutes, or between about 2-90 minutes, or between about 2-60 minutes, or between about 2-40 minutes, or between about 2-30 minutes, or between about 2-20 minutes, or about 2-10 minutes or between about 2-8 minutes, or between about 2-5 minutes; or 2 minutes, or 5 minutes or 10 minutes.

In certain instances, dissociation occurs in respect to temperature and does not require enzymes, chemicals, or amplification reaction conditions such as pH. In another embodiment, the modification group does not dissociate from a modified oligonucleotide below 70° C., or below 75° C., or below 80° C. or below 85° C., or below 90° C., or below 95° C.

Thermolabile modifications to an oligonucleotide primer can include the introduction of 4-oxo-1-pentyl (OXP) phosphotriester to the internucleotide linkage(s) of the oligonucleotide primer. The OXP can be introduced at the 3'-terminal internucleotide linkage or at the 3'-terminal and/or the 3'-penultimate internucleotide linkage. In other embodiments, the thermolabile modification to an oligonucleotide primer can include the introduction of 2-(N-formyl-N-methyl)aminotheyl (MAF) to the internucleotide linkage(s) of the oligonucleotide primer. The MAF can be introduced at the 3'-terminal internucleotide linkage or at the 3'-terminal and/or the 3'-penultimate internucleotide linkage. The conversion of OXP or MAF modified oligonucleotide primer to an unmodified primer is exploited to resolve amplicons derived from different templates in a mixed sample.

In some embodiments a method is disclosed, the method encompassing contacting a mixed sample with a first oligonucleotide primer and a second oligonucleotide primer, the first and second oligonucleotides primers priming amplification of a same target sequence with the second oligonucleotide primer having a modification, the modification being an OXP. Performing a nucleic acid amplification reaction, thereby forming a reacted sample and detecting an amplicon from a minor template. In some embodiments, the reacted mixed sample is subjected to a fractionation technique. In some embodiments, the fractionation technique is electrophoresis. In other embodiments, the fraction technique is mass spectrometry.

In other embodiments a method is disclosed, the method encompassing contacting a mixed sample with a first oligonucleotide primer and a second oligonucleotide primer, the first and second oligonucleotides primers priming amplification from a same target sequence with the second oligonucleotide primer having a modification, the modification being a MAF. Performing a nucleic acid amplification reaction, thereby forming a reacted sample and detecting an amplicon from a minor template. In some embodiments, the reacted mixed sample is subjected to a fractionation technique. In some embodiments, the fractionation technique is electrophoresis. In other embodiments, the fraction technique is mass spectrometry.

A "target species" is a polynucleotide sequence that is to be amplified. The target species is a nucleic acid sequence that is flanked by oligonucleotide primer binding sites. The target species can be a chromosomal locus, such as a gene or a short tandem repeat.

"Sample" refers to a solid or liquid suspected of containing a nucleic acid. Examples of a sample include whole blood, plasma, serum, saliva, sweat, vaginal secretions, vaginal cells, semen, tissues, urine or cerebrospinal fluid. A liquid culture medium used to grow cells can be a sample. The sample can be a filter paper upon which cells have been collected; for instance, buccal cells, blood cells, semen or vaginal fluids. The sample can be a filter paper having been contacted to a surface, for instance a surface on which there is a fingerprint. The sample can be cloth upon which cells have been deposited. For instance, the sample can be cloth upon which blood, saliva, semen or vaginal fluids have been applied. The sample can be a swab, or a portion thereof, upon which cells have collected; for instance, buccal cells, blood cells, semen or vaginal fluids. The swab can be made of materials such as cotton or Nylon™. The sample can be a swab having been contacted to a surface; for instance a surface on which there is a fingerprint, blood, saliva or vaginal fluids. The sample can be an extract derived from a filter paper or a swab contacted to cells; that is, filter paper or swabs upon which nucleic acid extraction methods have been applied so as to collect released nucleic acids.

The sample can be a mixed. That is, the sample can include solids or liquids or both suspected of containing a nucleic acid derived from more than one individual. For instance, a mixed sample can include vaginal secretions or vaginal cells and semen. Or for instance, a mixed sample can be cells from more than two persons. A mixed sample can, in some instances, be a population of the same cell type, members of which possessing allelic differences at the same target species. In some instances, the mixed sample can be a population of bacterial strains, algae species or viruses, as for example, in an environmental sample.

A "major template" is a nucleic acid present in the relatively greatest amount or concentration. In some instances, the major template is the nucleic acid that is relatively most readily amplified. The major template does not have to represent >50% of the nucleic acids in a sample, but be present in amounts greater than the next most prevalent species. For instance in instances when the nucleic acids from more than two individuals are present.

A "minor template" is a nucleic acid present in amounts relatively lower than the major template. In some instances, the minor template is the nucleic acid that is relatively less readily amplified.

In some embodiments a method is disclosed, the method entailing contacting a mixed sample with a first oligonucleotide primer and a second oligonucleotide primer, the first and second oligonucleotide primers priming amplification of a same target sequence, and performing a nucleic acid amplification reaction and thereby forming a reacted mixed sample. The first oligonucleotide primer is unlabeled while the second oligonucleotide primer is a modified oligonucleotide primer and is a detectable labeled. The label is detected in the reacted mixed sample, with the label attributable to an amplicon from a minor template being relatively greater than in reacted mixed sample encompassing the second oligonucleotide primer but the second oligonucleotide primer is not modified. In some embodiments, the first and the second oligonucleotide primers share identical nucleotide sequences. In other embodiments, the first and the second oligonucleotide primers share identical nucleotide sequences over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the first and the second oligonucleotide primers are the reverse complement of a sequence flanking the target sequence over a sequence of 5, 6, 7, 8, 9, 10, 11, 12, 13, 14, 15, 16, 17, 18, 19, 20, 21, 22, 23, 24, 25, 26, 27 or 28 nucleotides. In other embodiments, both the first and second oligonucleotide primers are labeled. In some embodiments, the reacted mixed sample is subjected to a fractionation technique. In some embodiments, the fractionation technique is electrophoresis. In other embodiments, the fraction technique is mass spectrometry.

In other embodiments a method is disclosed, the method entailing contacting a mixed sample with a first oligonucleotide primer and a second oligonucleotide primer, the first and second oligonucleotide primers priming amplification of a same target species, and performing a nucleic acid amplification reaction and thereby forming a reacted mixed sample. The first oligonucleotide primer is unlabeled while the second oligonucleotide primer is a modified oligonucleotide primer and has a detectable labeled, the modification being a thermolabile modification. In some embodiments, the thermolabile modification is OXP. In other embodiments, the thermolabile modification is MAF. The label is detected in the reacted mixed sample, with the label attributable to an amplicon from a minor template being relatively greater than in reacted mixed sample encompassing the second oligonucleotide primer but the second oligonucleotide primer is not modified. In some embodiments, the first and the second oligonucleotide primers share identical nucleotide sequences. In other embodiments, the first and the second oligonucleotide primers share identical nucleotide sequences over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the first and the second oligonucleotide primers are the reverse complement of a sequence flanking the target species over a sequence of 5, 6, 7, 8, 9, 10, 11, 12, 13, 14, 15, 16, 17, 18, 19, 20, 21, 22, 23, 24, 25, 26, 27 or 28 nucleotides. In other embodiments, both the first and second oligonucleotide primers are labeled. In some embodiments, the reacted mixed sample is subjected to a fractionation technique. In some embodiments, the fractionation technique is electrophoresis. In other embodiments, the fraction technique is mass spectrometry.

"Detectable Label" refers to moieties that be attached to nucleotides directly or indirectly to thereby render the molecule detectable by an instrument or method. For example, a label can be a moiety that: (i) provides a detectable signal or (ii) interacts with a second label to modify the detectable signal provided by the first or second label. Many different species of labels can be used, either individually or in combination with one or more different labels. A fluorophore is an example of a label.

In some embodiments, the first oligonucleotide primer possesses a detectable label. In other embodiments, the second oligonucleotide primer possesses a detectable label. In still other embodiments, the first and the second oligonucleotide primers each possess a detectable label. The detectable label can be the same or different on each oligonucleotide primer. In some embodiments, the first oligonucleotide primer but not the second oligonucleotide primer possesses a detectable label. In other embodiments, the second oligonucleotide primer but not first oligonucleotide primer possesses a detectable label.

In some embodiments, the first oligonucleotide primer possesses a fluorophore. In other embodiments, the second oligonucleotide primer possesses a fluorophore. In still other embodiments, the first and the second oligonucleotide primers each possess a fluorophore. The flourophore can be the same or different on each oligonucleotide primer. In some embodiments, the first oligonucleotide primer but not the second oligonucleotide primer possesses a fluorophore. In other embodiments, the second oligonucleotide primer but not first oligonucleotide primer possesses a fluorophore.

"Fluorophore" refers to a moiety that is inherently fluorescent or demonstrates a change in fluorescence upon binding to a biological compound or metal ion, or when metabolized by an enzyme. Numerous fluorophores are known, examples of which include coumarins, acridines, furans, dansyls, cyanines, pyrenes, naphthalenes, benzofurans, quinolines, quinazolinones, indoles, benzazoles, borapolyazaindacenes, oxazines and xanthenes, with the latter including fluoresceins, rhodamines, rosamines and rhodols.

In other embodiments a method is disclosed, the method entailing contacting a mixed sample with a first oligonucleotide primer and a second oligonucleotide primer, the first and second oligonucleotide primers priming amplification of a same target species, and performing a nucleic acid amplification reaction and thereby forming a reacted mixed sample. The label is detected in the reacted mixed sample, with the label attributable to an amplicon from a minor template being relatively greater than in reacted mixed sample encompassing the second oligonucleotide primer but the second oligonucleotide primer is not modified. The first oligonucleotide primer is unlabeled while the second oligonucleotide primer is a modified oligonucleotide primer and has a detectable labeled, the modification being a thermolabile modification. In some embodiments, the detectable label is a fluorophore. In other embodiments, the detectable label is a fluorescent dye. In some embodiments, the thermolabile modification is OXP. In other embodiments, the thermolabile modification is MAF. In some embodiments, the first and the second oligonucleotide primers share identical nucleotide sequences. In other embodiments, the first and the second oligonucleotide primers share identical nucleotide sequences over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the first and the second oligonucleotide primers are the reverse complement of a sequence flanking the target sequence over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the total number of target species amplified is less than 30, less than 29, less than 28, less than 27, less than 26, less than 24, less than 20. In some embodiments, the total number of target species amplified is from 1-100. In other embodiments, the total number of target species amplified is 2-100, or 5-75, or 10-50, or 13-26. In some embodiments, both the first and second oligonucleotide primers are labeled. In some embodiments, the reacted mixed sample is subjected to a fractionation technique. In some embodiments, the fractionation technique is electrophoresis. In other embodiments, the fraction technique is mass spectrometry.

In some embodiments, the first oligonucleotide primer possesses a fluorescent dye. In other embodiments, the second oligonucleotide primer possesses a fluorescent dye. In still other embodiments, the first and the second oligonucleotide primers each possess a fluorescent dye. The fluorescent dye can be the same or different on each oligonucleotide primer. In some embodiments, the first oligonucleotide primer but not the second oligonucleotide primer possesses a fluorescent dye. In other embodiments, the second oligonucleotide primer but not first oligonucleotide primer possesses a fluorescent dye.

Examples of fluorescent dyes, without limitation, include the following: 5- or 6-carboxyfluorescein (FAM™), VIC™ (a dye with a molecular weight of 550 and an absorbance maximum of 538 nm and an emission maximum of 554 nm), NED™, TAZ™, SID™, JOE™, TMR-ET, CXR-ET, BTG, BTY, BTR2, STP, BTO, fluorescein, fluorescein isothiocyanate (FITC), MD-700/800, cyanine dyes, such as CY3™, CY5™, CY3.5™, CY5.5™, Cy7™, xanthen, 6-carboxy-2',4',7',4,7-hexachlorofluorescein (HEX™), 6-carboxy-1,4-dichloro-2',7'-dichloro-fluorescein (TET®), 6-carboxy-4',5'-dichloro-2',7'-dimethodyfluorescein (JOE™), N,N,N',N'-tetramethyl-6-carboxyrhodamine (TAMRA™), 6-carboxy-X-rhodamine (ROX™), 5-carboxyrhodamine-6G (R6G5), 6-carboxyrhodamine-6G (RG6), rhodamine, rhodamine green, rhodamine red, rhodamine 110, Rhodamin 6G®, BODIPY dyes, such as BODIPY TMR, Oregon green, coumarines, such as umbelliferone, benzimides, such as Hoechst 33258; phenanthridines, such as Texas Red®, California Red®, Yakima Yellow, Alexa Fluor® 350, Alexa Fluor® 405, Alexa Fluor® 430, Alexa Fluor® 488, Alexa Fluor® 500, Alexa Fluor® 514, Alexa Fluor®532, Alexa Fluor® 546, Alexa Fluor® 555, Alexa Fluor® 568, Alexa Fluor® 594, Alexa Fluor® 610, Alexa Fluor® 633, Alexa Fluor® 647, Alexa Fluor® 660, Alexa Fluor® 680, Alexa Fluor® 700, Alexa Fluor® 750, PET®, ethidium bromide, acridinium dyes, carbazol dyes, phenoxazine dyes, porphyrine dyes, polymethin dyes, Atto 390, Atto 425, Atto 465, Atto 488, Atto 495, Atto 520, Atto 532, Atto 550, Atto 565, Atto 590, Atto 594, Atto 620, Atto 633, Atto 647N, Atto 655, Atto RhoG6, Atto Rho1 1, Atto Rho12, Atto Rho101, BMN™-5, BMN™-6, CEQ8000 D2, CEQ8000 D3, CEQ8000 D4, DY-480XL, DY-485XL, DY-495, DY-505, DY-510XL, DY-521XL, DY-521XL, DY-530, DY-547, DY-550, DY-555, DY-610, DY-615, DY-630, DY-631, DY-633, DY-635, DY-647, DY-651, DY-675, DY-676, DY-680, DY-681, DY-700, DY-701, DY-730, DY-731, DY-732, DY-750, DY-751, DY-776, DY-780, DY-781, DY-782, CAL Fluor® Gold 540, CAL Fluor RED 590, CAL Fluor Red 610, CAL Fluor Red 635, IRDye® 700Dx, IRDye® 800CW, Marina Blue®, Pacific Blue®, Yakima Yellow®, 6-(4,7-Dichloro-2',7'-diphenyl-3',6'-dipivaloylfluorescein-6-carboxamido)-hexyl-1-0-(2-cyanoethyl)-(N,N-diisopropyl)-phosphoramidite (SIMA), CAL Fluor® Gold 540, CAL Fluor® Orange 560, CAL Fluor Red 635, Quasar® 570, Quasar® 670, LIZ, Sunnyvale Red, LC Red® 610, LC Red® 640, LC Red®670 and LC Red®705.

In some embodiments the label is an affinity label. "Affinity label" refers to a moiety that specifically binds to a target molecule so that the target molecule can be captured, tracked or identified. Non-limiting examples of an affinity label are biotin, avidin, an antibody, an antigen, a receptor, a substrate, a lectin, an aptamer, a magnetically attractable solid support, or a magnet.

In some embodiments, the first oligonucleotide primer possesses an affinity label. In other embodiments, the second oligonucleotide primer possesses an affinity label. In still other embodiments, the first and the second oligonucleotide primers each possess an affinity label. The affinity label can be the same or different on each oligonucleotide primer. In some embodiments, the first oligonucleotide primer but not the second oligonucleotide primer possesses an affinity label. In other embodiments, the second oligonucleotide primer but not first oligonucleotide primer possesses an affinity label.

Forensics

A "short tandem repeat" (STR) is a genomic locus that contains repetitive sequence elements of from 2 to 7 nucleotides. Each sequence element, a repeat unit, is repeated at least once within an STR. Individuals can possess different numbers of repeat units and sequence variations at a STR locus. These differences are referred to as "alleles." Each STR locus often has multiple alleles. As the number of STR loci analyzed increases the probability that any two individuals will possess the same set of alleles becomes vanishingly small. Because of this, STR loci are preferred for determining identity because of the powerful statistical analysis that is possible with these markers.

It is estimated that over 100,000 STR loci exist in the human genome. Among this large number of STR loci, the U.S. forensics community has established a set of 13 human STR loci that can be used to develop a genetic profile for the identification of individuals. This set of 13 loci, often referred to as the "CODIS loci," includes the following STR loci: CSF1PO, FGA, THO1, TPDX, vWA, D3S1358, D5S818, D7S820, D8S1179, D13S317, D16S539, D18S51 and D21S11. Beyond the CODIS loci, other STR loci are routinely used for human identification purposes. These additional loci include D2S1338, D19S433, D12S391, D1S1656, D2S441, D10S1248, D22S1045, SE33, Penta D, Penta E and D6S1043. Information about these loci, such as the number of alleles and sequences, can be found, among other sources, at the STRbase on the world wide web.cstl.nist.gov/strbase.

STR analysis involves the multiplex amplification of a constellation of particular STR loci. The resulting amplified alleles are resolved by electrophoresis and the use of differential fluorescent dyes.

In the forensics context, mixed samples can be encountered in instances where there are multiple perpetrators or when a victim's and perpetrator's nucleic acids are comingled. Often under such circumstances, the nucleic acids from one individual are present in proportionally greater amounts than that of others. This can be problematic for forensics investigations utilizing amplified STRs since the genotypic signal from one individual will overwhelm that from others.

In some embodiments a method is disclosed, the method entailing contacting a mixed sample with a first oligonucleotide primer and a second oligonucleotide primer, the first and second oligonucleotide primers priming amplification of a same target species, the target species encompassing a STR locus and performing a nucleic acid amplification reaction and thereby forming a reacted mixed sample. The label is detected in the reacted mixed sample, with the label attributable to an amplicon from a minor template being relatively greater than in reacted mixed sample encompassing the second oligonucleotide primer but not the first oligonucleotide primer. In some embodiments, the target species encompasses one or more of the CODIS loci. In some embodiments, the target species encompasses one or more of the STR loci selected from D2S1338, D19S433, D12S391, D1S1656, D2S441, D10S1248, D22S1045, SE33, Penta D, Penta E and D6S1043. In some embodiments, the total number of target species amplified is less than 30, less than 29, less than 28, less than 27, less than 26, less than 24. In some embodiments, the total number of target species amplified is from 1-100. In other embodiments, the total number of target species amplified is 2-100, or 5-75, or 10-50, or 13-26. In some embodiments, the first oligonucleotide primer is unlabeled while the second oligonucleotide primer is a modified oligonucleotide primer and has a detectable labeled. In some embodiments, the detectable label is a fluorophore. In other embodiments, the detectable label is a fluorescent dye. In some embodiments the modification is a thermolabile modification. In some embodiments, the thermolabile modification is OXP. In other embodiments, the thermolabile modification is MAF. In some embodiments, the first and the second oligonucleotide primers share identical nucleotide sequences. In other embodiments, the first and the second oligonucleotide primers share identical nucleotide sequences over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the first and the second oligonucleotide primers are the reverse complement of a sequence flanking the target sequence over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, both the first and second oligonucleotide primers are labeled. In some embodiments, the reacted mixed sample is subjected to a fractionation technique. In some embodiments, the fractionation technique is electrophoresis. In other embodiments, the fraction technique is mass spectrometry.

The instant disclosure provides for an allelic ladder. "Allelic ladder" refers to a nucleic acid size standard that provides size standards for one or more alleles for a particular STR marker. The allelic ladder serves as a reference standard and nucleic acid size marker for the amplified alleles from the STR locus. In some embodiments, the allelic ladder can comprise size standards for the alleles of different STRs. In some embodiments, the allelic ladder can be made of DNA. In some embodiments the allelic ladder can be made of non-naturally occurring nucleic acid analogs. The different individual size standards within an allelic ladder can, in some embodiments can be labeled with a detectable label, for example, a fluorophore. In some embodiments, the allelic ladder components are labeled with the same fluorophore. In some embodiments, the allelic ladder components are labeled with the different fluorophores. The size standards can be selected to work for a specific pair (or pairs) of oligonucleotides primers. For example if a first set of primers for marker X produces a 150 base pair amplicon corresponding to allele 7, the corresponding marker will serve as a size standard for the 150 base amplicons; while a second pair of primers marker X produces a 175 base pair amplicon corresponding to allele 7, the corresponding marker will serve as a size standard for the 175 base amplicons. Thus different size standards for different size amplicons of the same allele are contemplated. The size standard for a given amplicon derived from a given allele may have nucleic acid base sequence that is the same or different than the nucleic acid base sequence of the amplicon or allele from which the amplicon is derived. For allele analysis in electrophoresis systems the size standard can be selected so as to have the same electrophoretic mobility as the amplicon of interest. Alternatively, in some embodiments, the size standard can be selected so as to have the different electrophoretic mobility than the amplicon of interest, given an understanding of the predicable nature of the difference, the identity of the amplicons could be determined. For allele analysis in mass spectroscopy systems the size standard (weight/charge ratio, not electrophoretic mobility) can be selected so as to have the same signal as the amplicon of interest. Alternatively, in some embodiments, the size standard (weight/charge ratio, not electrophoretic mobility) can be selected so as to have the different separation properties than the amplicon of interest, given an understanding of the predicable nature of the difference, the identity of the amplicons could be determined.

In some embodiments a method is disclosed, the method entailing contacting a mixed sample with a first oligonucleotide primer and a second oligonucleotide primer, the first and second oligonucleotide primers priming amplification of a same target species, the target species encompassing a STR locus and performing a nucleic acid amplification reaction and thereby forming a reacted mixed sample. The reacted mixed sample is subjected to a fractionation technique and compared to an allelic ladder. The label is detected in the reacted mixed sample, with the label attributable to an amplicon from a minor template being relatively greater than in reacted mixed sample encompassing the second oligonucleotide primer but not the first oligonucleotide primer. In some embodiments, the target species encompasses one or more of the CODIS loci. In some embodiments, the target species encompasses one or more of the STR loci selected from D2S1338, D19S433, D12S391, D1S1656, D2S441, D10S1248, D22S1045, SE33, Penta D, Penta E and D6S1043. In some embodiments, the total number of target species amplified is less than 30, less than 29, less than 28, less than 27, less than 26, less than 24. In some embodiments, the total number of target species amplified is from 1-100. In other embodiments, the total number of target species amplified is 2-100, or 5-75, or 10-50, or 13-26. In some embodiments, the first oligonucleotide primer is unlabeled while the second oligonucleotide primer is a modified oligonucleotide primer and has a detectable labeled. In some embodiments, the detectable label is a fluorophore. In other embodiments, the detectable label is a fluorescent dye. In some embodiments the modification is a thermolabile modification. In some embodiments, the thermolabile modification is OXP. In other embodiments, the thermolabile modification is MAF. In some embodiments, the first and the second oligonucleotide primers share identical nucleotide sequences. In other embodiments, the first and the second oligonucleotide primers share identical nucleotide sequences over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the first and the second oligonucleotide primers are the reverse complement of a sequence flanking the target sequence over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, both the first and second oligonucleotide primers are labeled. In some embodiments the fractionation technique is electrophoresis, for instance capillary electrophoresis.

A Composition

In some embodiments a composition is disclosed, the composition encompassing an unlabeled oligonucleotide primer and a labeled, modified oligonucleotide primer, each of the primers is the reverse complement over a span of at least 5 but less than 40 nucleotides of a same nucleic acid sequence, the nucleic acid sequence being within 10 kb, within 5 kb, within 2 kb, within 1 kb or within 500 bases of a target species. In some embodiments, both the first and the second primers will have the same nucleotide sequence. In some embodiments, each of the primers is less than 100 nucleotides, less than 90 nucleotides, less than 80 nucleotides, less than 70 nucleotides, less than 60 nucleotides, less than 50 nucleotides, less than 40 nucleotides, less than 30 nucleotides, less than 25 nucleotides. In some embodiments, the primers are from 18-40 nucleotides in length. In other embodiments, the first and the second oligonucleotide primers share identical nucleotide sequences over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the first and the second oligonucleotide primers are the reverse complement of a sequence flanking the target species over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the modification encompasses a thermolabile modification. In some embodiments, the thermolabile modification encompasses a 4-oxo-tetradecyl group. In other embodiments, the thermolabile modification encompasses a 2-(N-formyl-N-methyl) aminotheyl (MAF). In some embodiments, the target species is a short tandem repeat (STR) locus. In some embodiments, the STR locus encompasses one or more CODIS loci. In other embodiments, the STR locus encompasses one or more of D2S1338, D19S433, D12S391, D1S1656, D2S441, D10S1248, D22S1045, SE33, Penta D, Penta E and D6S1043. In some embodiments, the first oligonucleotide primer is unlabeled while the second oligonucleotide primer is a modified oligonucleotide primer and has a detectable labeled. In some embodiments, the detectable label is a fluorophore. In other embodiments, the detectable label is a fluorescent dye.

In some embodiments, the molar concentration of the first oligonucleotide primer and the second oligonucleotide primer are not the same.

The disclosed compositions can be applied in methods and as parts of kits.

A Kit

Disclosed herein are kits. "Kit" refers generally to a set of articles or implements which can be used in conjunction with one another to achieve a specific purpose.

In some embodiments, the kit encompasses a first primer and a second primer, the first primer and the second primer possess sequence that is the reverse complement of the same target sequence and the second primer possesses a modification. In some embodiments, the target sequence is a CODIS locus. In other embodiments, the target sequence is selected from D2S1338, D19S433, D12S391, D1S1656, D2S441, D10S1248, D22S1045, SE33, Penta D, Penta E and D6S1043. In some embodiments, the modification is a thermolabile modification. In other embodiments, the thermolabile modification is OXP. In some embodiments, the thermolabile modification is MAF.

In some embodiments, the kit also encompasses a container with a polymerase, a container with a first primer and a second primer and a container with a buffer, the first primer and the second primer possess a sequence that is the reverse complement of a sequence flanking an STR locus and the second primer also possesses a modification. In some embodiments, the target sequence is a CODIS locus. In other embodiments, the target sequence is selected from D2S1338, D19S433, D12S391, D1S1656, D2S441, D10S1248, D22S1045, SE33, Penta D, Penta E and D6S1043. In some embodiments, the modification is a thermolabile modification. In other embodiments, the thermolabile modification is OXP. In some embodiments, the thermolabile modification is MAF.

In other embodiments, the kit encompasses a container with an allelic ladder, a polymerase, a container with a first primer and a second primer and a container with a buffer, with the first primer and the second primer possessing a sequence that is the reverse complement of sequence flanking an STR locus and the second primer possesses a modification. In some embodiments, the modification is a thermolabile modification. In other embodiments, the thermolabile modification is OXP. In some embodiments, the thermolabile modification is MAF.

The primers can be maintained in the same container or in separate, individual containers. In some embodiments, both primers are in the same container. In other embodiments, one or more primers are in separate containers. In some embodiments, the first, the second or the first and the second primers are detectably labeled. In some embodiments, the first, the second or the first or the second primers are affinity labeled. In some embodiments, the first primer is affinity labeled and the second primer is detectably labeled.

In some embodiments there are oligonucleotide primers sufficient to amplify no more than 100 target species, no more than 95 target species, no more than 50 target species, no more than 35 target species, no more than 30 target species, no more than 25 target species, no more than 20 target species, no more than 15 target species, no more than 10 target species. In some embodiments, there are oligonucleotide primers sufficient to amplify from 1 to 100 target species. In some embodiments, there are oligonucleotide primers sufficient to amplify from 10 to 35 target species.

In some embodiments, there are less than 301 oligonucleotide primers. In some embodiments, there are less than 286 oligonucleotide primers. In some embodiments, there are less than 151 oligonucleotide primers. In some embodiments, there are less than 106 oligonucleotide primers. In some embodiments, there are less than 91 oligonucleotide primers. In some embodiments, there are less than 76 oligonucleotide primers. In some embodiments, there are less than 61 oligonucleotide primers. In some embodiments, there are less than 46 oligonucleotide primers and in some embodiments there are less than 31 oligonucleotide primers. In some embodiments there are more than 29 oligonucleotide primers and less than 301. In other embodiments, there are more than 29 oligonucleotide primers but less than 91 primers.

In some embodiments, the first oligonucleotide primer is unlabeled while the second oligonucleotide primer is a modified oligonucleotide primer and has a detectable labeled. In some embodiments, the detectable label is a fluorophore. In other embodiments, the detectable label is a fluorescent dye.

In some embodiments the modification is a thermolabile modification. In some embodiments, the thermolabile modification is OXP. In other embodiments, the thermolabile modification is MAF. In some embodiments, the first and the second oligonucleotide primers share identical nucleotide sequences. In other embodiments, the first and the second oligonucleotide primers share identical nucleotide sequences over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, the first and the second oligonucleotide primers are the reverse complement of a sequence flanking the target sequence over a sequence of 5, 6, 7, 8, 9, 10, 11, 12, 13, 14, 15, 16, 17, 18, 19, 20, 21, 22, 23, 24, 25, 26, 27 or 28 nucleotides. In some embodiments, both the first and second oligonucleotide primers are labeled.

EXAMPLES

Enrichment for a Male Autosomal Short Tandem Repeat Profile in the Presence of Excess Female DNA The relative enrichment for a male derived short tandem repeat profile in the presence of excess female DNA is accomplished using modified oligonucleotides primers. Male DNA 9948 (Origene, Rockville, Md.) is mixed in a dilution series with Female 9947A (Origene, Rockville, Md.). The final ratios of male to female DNA in the dilution series are from 1:1, 1:5, 1:10, 1:100 and 1:1000. 1 ng. of total DNA from each dilution is used as template for the amplification of STR loci by multiplex PCR.

All the amplification reactions contain 1×PCR buffer [20 mM Tris.HCl (pH 8.4), 50 mM KCl, 2.5 mM $MgCl_2$], 0.2 mM dNTPs and 1.25 U recombinant Taq DNA polymerase in a 25 µl total reaction volume. Each STR locus is amplified with a primer pair, with one primer of the pair being modified with OXP. The thermal cycling conditions are: 94° C. for 10 minutes, 29 cycles [94° C. for 20 seconds, 59° C. for 30 seconds, 72° C. for 30 seconds], and final extension at 72° C. for 15 minutes. The final products are subjected to capillary electrophoresis.

Each sample for analysis is prepared by adding 1 µl. of the final reaction product to 19 µl. of Hi-Di formamide (Applied Biosystems) containing 0.75 µl. of GS500ROX size standard (Applied Biosystems). Samples are placed immediately into the instrument for analysis without heat denaturation or snap cooling. Samples are injected for 5 s at 15 kV and separated at 15 kV for 24 min with a run temperature of 60° C. Standard electrophoretic conditions are used including buffer and polymer.

I claim:
1. A method comprising:
a) contacting a mixed sample comprising a major template and a minor template with a first oligonucleotide primer and a second oligonucleotide primer, the second oligonucleotide primer is labeled and comprises a modification, the modification comprising a 4-oxo-tetradecyl group or a 2-(N-formyl-N-methyl)aminotheyl group or both, the first and second oligonucleotides primers priming amplification of a same target species, the target species being a short tandem repeat (STR);
b) performing a nucleic acid amplification reaction and thereby forming a reacted mixed sample;
c) subjecting the reacted mixed sample to capillary electrophoresis; and
d) detecting and comparing a labeled product from the reacted mixed sample to an allelic ladder, the label attributable to an amplicon from a minor template being relatively greater than in an amplification reaction comprising the first oligonucleotide primer and the second oligonucleotide primer without a 4-oxo-tetradecyl group or a 2-(N-formyl-N-methyl)aminotheyl group or both.

2. The method of claim 1, wherein the label is a fluorescent label.

3. The method of claim 1, wherein the STR is a CODIS locus.

4. The method of claim 1, wherein the STR is D2S1338, D19S433, D12S391, D1S1656, D2S441, D10S1248, D22S1045, SE33, Penta D, Penta E or D6S1043.

5. The method of claim 1, wherein the first oligonucleotide primer and the second oligonucleotide primer have the exact same nucleotide sequence.

6. The method of claim 1, wherein the molar concentration of the first oligonucleotide primer and the second oligonucleotide primer are not the same.

* * * * *